(12) United States Patent
Callahan et al.

(10) Patent No.: US 9,439,755 B2
(45) Date of Patent: Sep. 13, 2016

(54) HAPTIC DEVICES FOR INTRAOCULAR LENS

(75) Inventors: Wayne B. Callahan, Abingdon, VA (US); Paul S. Koch, Warwick, RI (US); Anna S. Hayes, Newton Centre, MA (US); Robert E. Kellan, Methuen, MA (US)

(73) Assignee: Anew IOL Technologies, Inc., Bristol, TN (US)

( * ) Notice: Subject to any disclaimer, the term of this patent is extended or adjusted under 35 U.S.C. 154(b) by 0 days.

(21) Appl. No.: 12/626,473

(22) Filed: Nov. 25, 2009

(65) Prior Publication Data

US 2010/0131061 A1    May 27, 2010

Related U.S. Application Data

(60) Provisional application No. 61/118,085, filed on Nov. 26, 2008, provisional application No. 61/157,781, filed on Mar. 5, 2009, provisional application No. 61/184,655, filed on Jun. 5, 2009.

(51) Int. Cl.
*A61F 2/16*    (2006.01)

(52) U.S. Cl.
CPC ........ *A61F 2/1613* (2013.01); *A61F 2002/169* (2015.04); *A61F 2002/1681* (2013.01)

(58) Field of Classification Search
CPC ................. A61F 2002/1681–2002/169053
USPC .................................. 623/6.38–6.55
See application file for complete search history.

(56) References Cited

U.S. PATENT DOCUMENTS

| | | |
|---|---|---|
| 3,673,616 A | 7/1972 | Fedorov et al. |
| 3,866,249 A | 2/1975 | Flom |
| 3,906,551 A | 9/1975 | Otter |
| 3,913,148 A | 10/1975 | Potthast |

(Continued)

FOREIGN PATENT DOCUMENTS

| | | |
|---|---|---|
| EP | 1961399 | 4/1991 |
| GB | 2029235 | 3/1980 |

(Continued)

OTHER PUBLICATIONS

Chinese Office Action for Chinese Application 200780020967.4 dated Apr. 12, 2011.

(Continued)

*Primary Examiner* — Andrew Iwamaye
*Assistant Examiner* — Leslie Lopez
(74) *Attorney, Agent, or Firm* — Remenick PLLC

(57) ABSTRACT

The inventive is directed to a haptic for fixation to, and manufacture in conjunction with, an intraocular lens to be implanted in the natural lens capsule of the human eye. The haptic secures the lens in an appropriate position within the natural capsule so as to provide optimal visual acuity through the aphakic lens. The haptic ends are designed to position the lens neutrally, anteriorly or posteriorly within the lens envelope. At the connection point of the ribbon portion to the solid end plate of the haptic, the haptic may be notched to facilitate compressing the lens into its injector for insertion into the eye through an incision in the cornea. Once compressed and passed through the cornea, the implanted lens will be secured by the haptics in the lens capsule once all possible natural lens material and epithelial cells have been removed.

22 Claims, 14 Drawing Sheets

(56) References Cited

U.S. PATENT DOCUMENTS

| | | | |
|---|---|---|---|
| 3,975,779 A | 8/1976 | Richards et al. | |
| 4,014,049 A | 3/1977 | Richards et al. | |
| 4,053,953 A | 10/1977 | Flom et al. | |
| 4,073,014 A | 2/1978 | Poler | |
| 4,087,866 A | 5/1978 | Choyce et al. | |
| 4,092,743 A | 6/1978 | Kelman | |
| 4,102,567 A | 7/1978 | Cuffe et al. | |
| 4,136,406 A | 1/1979 | Norris | |
| 4,141,973 A | 2/1979 | Balazs | |
| 4,159,546 A | 7/1979 | Shearing | |
| 4,173,281 A | 11/1979 | Trought | |
| 4,174,543 A | 11/1979 | Kelman | |
| 4,190,049 A | 2/1980 | Hager et al. | |
| 4,198,980 A | 4/1980 | Clark | |
| 4,215,440 A | 8/1980 | Worst | |
| 4,240,163 A | 12/1980 | Galin | |
| 4,242,760 A | 1/1981 | Rainin | |
| 4,244,060 A | 1/1981 | Hoffer | |
| 4,249,271 A | 2/1981 | Poler | |
| 4,251,887 A | 2/1981 | Anis | |
| 4,254,509 A | 3/1981 | Tennant | |
| 4,254,510 A | 3/1981 | Tennant | |
| 4,269,307 A | 5/1981 | LaHaye | |
| 4,270,230 A | 6/1981 | Poler | |
| 4,280,232 A | 7/1981 | Hummel | |
| 4,285,072 A | 8/1981 | Morcher et al. | |
| 4,325,375 A | 4/1982 | Nevyas | |
| 4,326,306 A | 4/1982 | Poler | |
| 4,349,027 A | 9/1982 | DiFrancesco | |
| 4,363,142 A | 12/1982 | Meyer | |
| 4,363,143 A | 12/1982 | Callahan | |
| 4,366,582 A | 1/1983 | Faulkner | |
| 4,370,760 A | 2/1983 | Kelman | |
| 4,377,329 A * | 3/1983 | Poler | 351/159.02 |
| 4,409,691 A | 10/1983 | Levy | |
| 4,423,809 A | 1/1984 | Mazzocco | |
| 4,435,855 A | 3/1984 | Pannu | |
| 4,441,217 A | 4/1984 | Cozean, Jr. | |
| 4,446,581 A | 5/1984 | Blake | |
| 4,451,938 A | 6/1984 | Kelman | |
| 4,463,458 A | 8/1984 | Seidner | |
| 4,468,820 A | 9/1984 | Uhler et al. | |
| 4,480,340 A | 11/1984 | Shepard | |
| 4,494,254 A | 1/1985 | Lopez | |
| 4,504,981 A | 3/1985 | Walman | |
| 4,508,216 A | 4/1985 | Kelman | |
| 4,517,295 A | 5/1985 | Bracke et al. | |
| 4,527,294 A | 7/1985 | Heslin | |
| 4,530,117 A | 7/1985 | Kelman | |
| 4,534,069 A | 8/1985 | Kelman | |
| 4,536,895 A | 8/1985 | Bittner | |
| 4,573,998 A | 3/1986 | Mazzocco | |
| 4,575,374 A | 3/1986 | Anis | |
| 4,576,607 A | 3/1986 | Kelman | |
| 4,581,033 A | 4/1986 | Callahan | |
| 4,585,456 A | 4/1986 | Blackmore | |
| 4,591,358 A | 5/1986 | Kelman | |
| 4,608,049 A | 8/1986 | Kelman | |
| 4,615,703 A | 10/1986 | Callahan et al. | |
| 4,619,256 A | 10/1986 | Horn | |
| 4,624,669 A | 11/1986 | Grendahl | |
| 4,629,460 A | 12/1986 | Dyer | |
| 4,634,423 A | 1/1987 | Bailey, Jr. | |
| 4,638,056 A | 1/1987 | Callahan et al. | |
| 4,655,775 A | 4/1987 | Clasby, III | |
| 4,676,792 A | 6/1987 | Praeger | |
| 4,676,794 A | 6/1987 | Kelman | |
| 4,684,014 A | 8/1987 | Davenport | |
| 4,687,484 A | 8/1987 | Kaplan | |
| 4,700,638 A | 10/1987 | Przewalski | |
| 4,701,181 A | 10/1987 | Arnott | |
| 4,704,123 A | 11/1987 | Smith | |
| 4,710,195 A | 12/1987 | Giovinazzo | |
| 4,710,795 A | 12/1987 | Nippert et al. | |
| 4,711,638 A | 12/1987 | Lindstrom | |
| 4,718,906 A | 1/1988 | Mackool | |
| 4,736,836 A | 4/1988 | Alongi et al. | |
| 4,764,169 A | 8/1988 | Grendahl | |
| 4,769,035 A | 9/1988 | Kelman | |
| 4,778,464 A | 10/1988 | Sergienko et al. | |
| 4,781,719 A | 11/1988 | Kelman | |
| 4,787,902 A | 11/1988 | Sheets et al. | |
| 4,795,460 A | 1/1989 | Anis | |
| 4,795,462 A | 1/1989 | Grendahl | |
| 4,804,361 A | 2/1989 | Anis | |
| 4,816,032 A | 3/1989 | Hetland | |
| 4,828,558 A | 5/1989 | Kelman | |
| 4,834,750 A | 5/1989 | Gupta | |
| 4,842,600 A | 6/1989 | Feaster | |
| RE33,039 E | 8/1989 | Arnott | |
| 4,852,566 A | 8/1989 | Callahan et al. | |
| 4,863,462 A | 9/1989 | Fedorov et al. | |
| 4,863,463 A | 9/1989 | Tjan | |
| 4,863,465 A | 9/1989 | Kelman | |
| 4,871,363 A | 10/1989 | Kelman | |
| 4,872,876 A | 10/1989 | Smith | |
| 4,878,911 A | 11/1989 | Anis | |
| 4,888,012 A | 12/1989 | Horn | |
| 4,919,130 A | 4/1990 | Stoy et al. | |
| 4,923,296 A | 5/1990 | Erickson | |
| 4,932,966 A * | 6/1990 | Christie | A61F 2/1613 623/6.13 |
| 4,932,970 A | 6/1990 | Portney | |
| 4,950,290 A | 8/1990 | Kamerling | |
| 4,994,080 A | 2/1991 | Shepard | |
| 4,995,714 A | 2/1991 | Cohen | |
| 5,002,568 A | 3/1991 | Katzen | |
| 5,019,098 A | 5/1991 | Mercier | |
| 5,047,052 A | 9/1991 | Dubroff | |
| 5,076,684 A | 12/1991 | Simpson et al. | |
| 5,098,444 A | 3/1992 | Feaster | |
| 5,100,226 A | 3/1992 | Freeman | |
| 5,108,429 A | 4/1992 | Wiley | |
| 5,118,452 A | 6/1992 | Lindsey et al. | |
| 5,123,905 A | 6/1992 | Kelman | |
| 5,133,747 A | 7/1992 | Feaster | |
| 5,133,749 A | 7/1992 | Nordan | |
| 5,152,789 A * | 10/1992 | Willis | 623/6.4 |
| 5,166,711 A | 11/1992 | Portney | |
| 5,171,320 A | 12/1992 | Nishi | |
| 5,176,686 A | 1/1993 | Poley | |
| 5,178,636 A | 1/1993 | Silberman | |
| 5,192,319 A | 3/1993 | Worst | |
| 5,197,981 A | 3/1993 | Southard | |
| 5,199,559 A | 4/1993 | Dark | |
| 5,229,797 A | 7/1993 | Futhey et al. | |
| 5,236,452 A | 8/1993 | Nordan | |
| 5,258,025 A | 11/1993 | Fedorov et al. | |
| 5,266,074 A | 11/1993 | Nishi et al. | |
| 5,281,227 A | 1/1994 | Sussman | |
| 5,361,780 A | 11/1994 | Kellan | |
| 5,366,501 A | 11/1994 | Langerman | |
| 5,370,652 A | 12/1994 | Kellan | |
| 5,405,386 A | 4/1995 | Rheinish et al. | |
| 5,425,734 A | 6/1995 | Blake | |
| D360,068 S | 7/1995 | Hambleton et al. | |
| 5,443,506 A | 8/1995 | Garabet | |
| 5,468,246 A | 11/1995 | Blake | |
| 5,476,512 A | 12/1995 | Sarfarazi | |
| 5,476,514 A | 12/1995 | Cumming | |
| 5,480,428 A | 1/1996 | Fedorov et al. | |
| 5,489,302 A | 2/1996 | Skottun | |
| 5,496,366 A | 3/1996 | Cumming | |
| 5,507,806 A | 4/1996 | Blake | |
| 5,522,890 A | 6/1996 | Nakajima et al. | |
| 5,549,670 A | 8/1996 | Young et al. | |
| 5,593,436 A | 1/1997 | Langerman | |
| 5,628,794 A | 5/1997 | Lindstrom | |
| 5,643,275 A | 7/1997 | Blake | |
| D382,399 S | 8/1997 | Hambleton et al. | |
| 5,674,282 A | 10/1997 | Cumming | |
| 5,682,223 A | 10/1997 | Menezes et al. | |
| 5,697,973 A * | 12/1997 | Peyman et al. | 623/6.26 |
| 5,709,220 A | 1/1998 | Kellan | |

(56) References Cited

U.S. PATENT DOCUMENTS

| | | |
|---|---|---|
| 5,713,958 A | 2/1998 | Weiser |
| 5,772,667 A | 6/1998 | Blake |
| 5,782,911 A | 7/1998 | Herrick |
| 5,800,532 A | 9/1998 | Lieberman |
| 5,847,802 A | 12/1998 | Menezes et al. |
| 5,855,605 A | 1/1999 | Herrick |
| 5,919,229 A | 7/1999 | Portney |
| 5,928,282 A | 7/1999 | Nigam |
| 5,947,976 A | 9/1999 | Van Noy et al. |
| 5,976,150 A | 11/1999 | Copeland |
| 6,010,510 A | 1/2000 | Brown |
| 6,013,101 A | 1/2000 | Israel |
| 6,015,435 A | 1/2000 | Valunin et al. |
| 6,051,024 A | 4/2000 | Cumming |
| 6,083,261 A | 7/2000 | Callahan et al. |
| 6,090,141 A | 7/2000 | Lindstrom |
| 6,096,077 A | 8/2000 | Callahan et al. |
| 6,110,202 A | 8/2000 | Barraquer et al. |
| 6,120,148 A | 9/2000 | Fiala et al. |
| 6,129,723 A | 10/2000 | Anderson |
| 6,142,999 A | 11/2000 | Brady et al. |
| 6,152,958 A | 11/2000 | Nordan |
| 6,197,059 B1 | 3/2001 | Cumming |
| 6,203,549 B1 | 3/2001 | Waldock |
| 6,224,628 B1 | 5/2001 | Callahan et al. |
| 6,241,777 B1 | 6/2001 | Kellan |
| 6,261,321 B1 | 7/2001 | Kellan |
| 6,277,146 B1 | 8/2001 | Peyman et al. |
| 6,299,641 B1 | 10/2001 | Woods |
| 6,398,786 B1 | 6/2002 | Sesic |
| 6,443,985 B1 | 9/2002 | Woods |
| 6,447,519 B1 | 9/2002 | Brady |
| 6,461,384 B1 | 10/2002 | Hoffmann |
| 6,488,707 B1 | 12/2002 | Callahan et al. |
| 6,488,709 B1 | 12/2002 | Barrett |
| 6,494,911 B2 | 12/2002 | Cumming |
| 6,517,577 B1 | 2/2003 | Callahan et al. |
| 6,533,813 B1 | 3/2003 | Lin et al. |
| 6,537,283 B2 | 3/2003 | Van Noy |
| 6,605,093 B1 | 8/2003 | Blake |
| 6,622,855 B1 | 9/2003 | Callahan et al. |
| 6,623,522 B2 | 9/2003 | Nigam |
| 6,645,246 B1 | 11/2003 | Weinschenk, III |
| 6,666,887 B1 | 12/2003 | Callahan et al. |
| 6,749,633 B1* | 6/2004 | Lorenzo ............ A61F 2/1602 623/6.28 |
| 6,786,928 B2 | 9/2004 | Callahan et al. |
| 6,797,004 B1 | 9/2004 | Brady |
| 6,800,091 B2 | 10/2004 | Callahan et al. |
| 6,921,415 B2 | 7/2005 | Callahan et al. |
| 6,976,989 B1 | 12/2005 | Vincent |
| 7,037,328 B2 | 5/2006 | Vincent |
| 7,037,338 B2 | 5/2006 | Nagamoto |
| 7,063,723 B2 | 6/2006 | Ran |
| 7,125,422 B2 | 10/2006 | Woods |
| 7,179,292 B2 | 2/2007 | Worst |
| 7,198,640 B2 | 4/2007 | Nguyen |
| 7,220,279 B2 | 5/2007 | Nun |
| 7,223,288 B2 | 5/2007 | Zhang |
| 7,279,006 B2 | 10/2007 | Vincent |
| 7,354,451 B2 | 4/2008 | Koch |
| 7,503,938 B2 | 3/2009 | Phillips |
| 7,713,299 B2 | 5/2010 | Brady et al. |
| 8,043,372 B2 | 10/2011 | Bumbalough |
| 2001/0001836 A1 | 5/2001 | Cumming |
| 2001/0012964 A1 | 8/2001 | Lang |
| 2001/0044657 A1 | 11/2001 | Kellan |
| 2001/0044857 A1 | 11/2001 | Pham et al. |
| 2002/0055777 A1 | 5/2002 | Cumming et al. |
| 2002/0072673 A1 | 6/2002 | Yamamoto |
| 2002/0072795 A1 | 6/2002 | Green |
| 2002/0095212 A1 | 7/2002 | Boehm |
| 2002/0103536 A1 | 8/2002 | Landreville et al. |
| 2002/0116059 A1 | 8/2002 | Zadno-Azizi et al. |
| 2002/0120331 A1 | 8/2002 | Galin et al. |
| 2002/0161437 A1 | 10/2002 | Zhou et al. |
| 2002/0193877 A1 | 12/2002 | Hoffmann et al. |
| 2003/0033013 A1 | 2/2003 | Callahan |
| 2003/0050695 A1 | 3/2003 | Lin et al. |
| 2003/0065387 A1 | 4/2003 | Callahan et al. |
| 2003/0078655 A1 | 4/2003 | Callahan |
| 2003/0114927 A1 | 6/2003 | Nagamoto |
| 2003/0130732 A1 | 7/2003 | Sarfarazi |
| 2003/0135272 A1 | 7/2003 | Brady et al. |
| 2003/0135273 A1 | 7/2003 | Callahan |
| 2003/0149479 A1 | 8/2003 | Snyder et al. |
| 2003/0149480 A1 | 8/2003 | Shadduck et al. |
| 2004/0215340 A1 | 10/2004 | Messner et al. |
| 2004/0230300 A1 | 11/2004 | Bandhauer et al. |
| 2004/0236423 A1 | 11/2004 | Zhang et al. |
| 2004/0249456 A1 | 12/2004 | Cumming |
| 2005/0033308 A1 | 2/2005 | Callahan |
| 2005/0107875 A1 | 5/2005 | Cumming |
| 2005/0251253 A1 | 11/2005 | Gross |
| 2006/0047339 A1 | 3/2006 | Brown |
| 2006/0047340 A1 | 3/2006 | Brown |
| 2006/0100704 A1* | 5/2006 | Blake et al. ............. 623/6.37 |
| 2006/0142781 A1 | 6/2006 | Pynson et al. |
| 2006/0235515 A1 | 10/2006 | Chassain |
| 2006/0247767 A1 | 11/2006 | Koch |
| 2006/0293694 A1 | 12/2006 | Futamura |
| 2007/0093892 A1 | 4/2007 | Mackool |
| 2007/0129799 A1* | 6/2007 | Schedler ............ A61F 2/1613 623/6.13 |
| 2007/0135915 A1* | 6/2007 | Klima ............ 623/6.37 |
| 2007/0156236 A1* | 7/2007 | Stenger ............ 623/6.13 |
| 2007/0239274 A1 | 10/2007 | Kellan |
| 2007/0260309 A1* | 11/2007 | Richardson ............. 623/6.34 |
| 2008/0161913 A1 | 7/2008 | Brady et al. |
| 2008/0281417 A1 | 11/2008 | Nagamoto |
| 2009/0125106 A1* | 5/2009 | Weinschenk et al. ....... 623/6.32 |
| 2009/0171458 A1 | 7/2009 | Kellan et al. |
| 2009/0248031 A1 | 10/2009 | Ichinohe et al. |
| 2010/0131059 A1 | 5/2010 | Callahan et al. |
| 2010/0131061 A1 | 5/2010 | Callahan et al. |
| 2010/0179652 A1 | 7/2010 | Yamamoto |
| 2010/0204787 A1 | 8/2010 | Noy |
| 2010/0204788 A1 | 8/2010 | Van Noy |
| 2010/0228260 A1 | 9/2010 | Callahan et al. |
| 2011/0054600 A1 | 3/2011 | Bumbalough |
| 2011/0191086 A1 | 8/2011 | Callahan |
| 2011/0257742 A1 | 10/2011 | Bumbalough |
| 2011/0313522 A1 | 12/2011 | Hayes |
| 2011/0313523 A1 | 12/2011 | Hayes |
| 2012/0010704 A1 | 1/2012 | Bumbalough |
| 2012/0078363 A1 | 3/2012 | Lu |
| 2012/0330415 A1 | 12/2012 | Callahan et al. |

FOREIGN PATENT DOCUMENTS

| | | |
|---|---|---|
| GB | 2124500 | 2/1984 |
| GB | 2165456 | 4/1986 |
| JP | 61502661 | 11/1985 |
| JP | 6055131 | 12/1985 |
| JP | 2003533274 | 11/2003 |
| WO | WO98/17205 | 4/1998 |
| WO | WO99/29266 | 6/1999 |
| WO | WO00/78252 | 12/2000 |
| WO | WO03017867 | 6/2003 |
| WO | WO2004082535 | 9/2004 |
| WO | WO2007117476 | 10/2007 |
| WO | WO2007134019 | 11/2007 |
| WO | WO2008108523 | 9/2008 |
| WO | WO2008108524 | 9/2008 |

OTHER PUBLICATIONS

Austria Examination Report for Austrian Application 200807369-4 dated Mar. 10, 2010.
PCT Search Report for PCT/US2009/065955 dated May 31, 2011.
PCT Patentability Report for PCT/US2009/065955 dated Jan. 27, 2010.
PCT Search Report for PCT/US2009/065960 dated Jan. 27, 2010.

(56) References Cited

OTHER PUBLICATIONS

PCT Patentability Report for PCT/US2009/065960 dated Jan. 27, 2010.
PCT Search Report for PCT/US2007/008328 dated Jun. 19, 2008.
PCT Patentability Report for PCT/US2007/008328 dated Jun. 19, 2008.
PCT Search Report for PCT/US2008/088430 dated Aug. 11, 2009.
PCT Patentability Report for PCT/US2008/088430 dated Aug. 11, 2009.
PCT Search Report for PCT/US2010/026230 dated May 19, 2010.
PCT Patentabilty Report for PCT/US2010/026230 dated May 19, 2010.
PCT Search Report for PCT/US2006/16221 dated May 10, 2007.
PCT Patentability Report for PCT/US2006/16221 dated May 10, 2007.
PCT Search Report for PCT/US2011/37583 dated Nov. 15, 2011.
PCT Patentabilty Report for PCT/US2011/37583 dated Nov. 15, 2011.
Zaldivar et al,; "The Current Status of Phakic Intraocular Lenses;" International Opthamology Clinics; vol. 36, No. 4; 1996; pp. 107-111.
Neuhann; "Corneal or Lens Refractive Surgery?" Journal of Refractive Surgery; vol. 14; May/Jun. 1998; pp. 272-279.
Rosen et al.; "Staar Collamer Posterior Chamber Phakic Intraocular Lens to Correct Myopia and Hyperopia;" J. Cataract Refract. Surg.; vol. 24; May 1998; pp. 596-606.
Sanders et al; "Implantable Contact Lens for Moderate to High Myopia: Phase 1 FDA Clinical Study with 6 Month Follow-Up;" J. Cataract Refract Surg.; vol. 24; May 1998; pp. 607-6111.
PCT Search Report for PCT/US2010/026230, dated May 19, 2010.
PCT Patentability Report for PCT/US2010/026230, dated May 19, 2010.
PCT Patentability Report for PCT/US2009/065955, dated Jan. 27, 2010.
PCT Search Report for PCT/US2009/065955, dated Jan. 27, 2010.
Japan Office Action for Japanese Application 2009-504268, dated Apr. 24, 2012.
Chinese Decision of Rejection for Chinese Application 200780020967.4, dated May 28, 2012.
Australian Examination Report for Austrian Application 2009319753, dated Aug. 29, 2012.
PCT Search Report and Patentability Report for PCT/US12/40732, dated Sep. 18, 2012.
CA Office Action for Application No. 2,744,859, dated Sep. 11, 2012.
PCT Search Report for PCT/US2012/072014, dated Mar. 8, 2013.

* cited by examiner

Figure 13
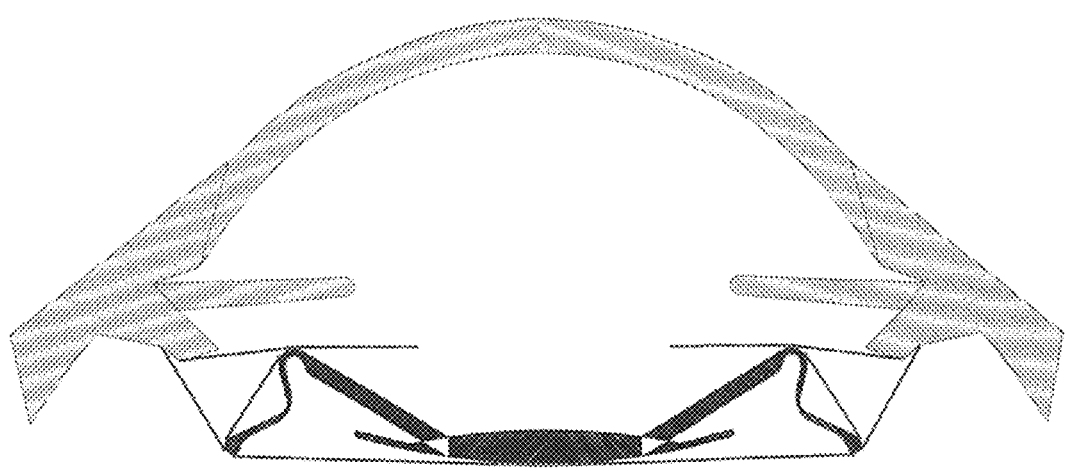
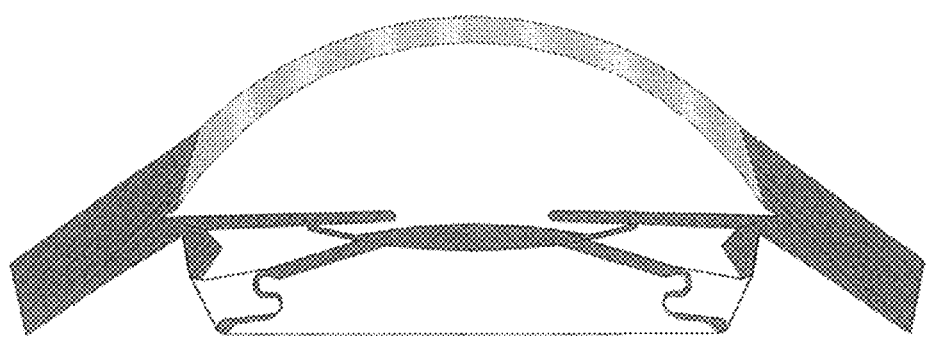
Figure 14

HAPTIC DEVICES FOR INTRAOCULAR LENS

REFERENCE TO RELATED APPLICATIONS

This application claims priority to U.S. Provisional Application No. 61/118,085 of the same title and filed Nov. 26, 2008, U.S. Provisional Application No. 61/157,781 of the same title and filed Mar. 5, 2009, and U.S. Provisional Application No. 61/184,655 of the same title and filed Jun. 5, 2009, the entirety of each of which is hereby incorporated by reference.

BACKGROUND

1. Field of the Invention

This invention is directed to haptic devices for intraocular lenses that provide increased comfort and performance to a patient. In particular, the invention is directed to haptic devices and designs, including injectors, for insertion of intraocular lenses without rolling the lenses, and to methods for performing insertion. Specifically, the invention, along with its various iterations, is designed to provide suitable degrees of focal flexibility, or accommodation, when used in conjunction with a monofocal optic, and, in certain instances, mitigate the onset of post-surgical conditions, specifically posterior capsular Opacification.

2. Description of the Background

An intraocular lens (IOL) is an implanted lens in the eye, usually replacing the existing crystalline lens because it has been clouded over by a cataract, or as a form of refractive surgery to change the eye's optical power. The whole device usually comprises a small plastic lens with plastic side struts, called haptics, to hold the lens in place within the capsular bag inside the eye. Haptics also form the means of attachment of lenses to other areas of the eye, including the anterior angle or sulcus, the iris, and the posterior chamber ciliary sulcus. IOLs were traditionally made of an inflexible material (e.g. PMMA) though this largely been superseded by the use of flexible materials. Most IOLs fitted today are fixed monofocal lenses matched to distance vision. However, other types are available, such as multifocal IOLs which provide the patient with multiple-focused vision at far and reading distance, tonic IOLs to correct for astigmatisms, and adaptive IOLs which provide the patient with limited visual accommodation.

Intraocular lenses have been used since 1999 for correcting larger errors in myopic (near-sighted), hyperopic (far-sighted), and astigmatic eyes. This type of IOL is also called PIOL (phakic intraocular lens), and the crystalline lens is not removed. More commonly, aphakic IOLs (that is, not PIOLs) are now used for visual correction errors (especially substantial hyperopia), and implanted via Clear Lens Extraction and Replacement (CLEAR) surgery. During CLEAR, the crystalline lens is extracted and an IOL replaces it in a process that is very similar to cataract surgery: both involve lens replacement, local anesthesia, both last approximately 30 minutes, and both require making a small incision in the eye for lens insertion. Patients recover from CLEAR surgery 1-7 days after the operation. During this time, patients should avoid strenuous exercise or any activity that significantly raises blood pressure. Patients should also visit their ophthalmologists regularly for several months so as to monitor the IOL implants. CLEAR has a 90% success rate (risks include wound leakage, infection, inflammation, and astigmatism). CLEAR can only be performed on patients ages 40 and older. This is to ensure that eye growth, which disrupts IOL lenses, will not occur post-surgery.

Once implanted, IOL lenses have three major benefits. First, they are an alternative to LASIK, a form of eye surgery that does not work for people with serious vision problems. Second, effective IOL implants may eliminate the need for glasses or contact lenses post-surgery. Third, the cataract will not return, as the lens has been removed. The disadvantage is that the eye's ability to change focus (accommodate) may have been reduced or eliminated, depending on the kind of lens implanted.

While significant advances have been made in the optical quality of aphakic lenses, most lenses currently made have an overall optical thickness of one millimeter or greater at the center optical focal point (e.g. see U.S. Pat. No. 4,363, 142). In the late 1990's, two patents were applied for and subsequently issued for lens optics significantly thinner than the afore-referenced lens patents (U.S. Pat. Nos. 6,096,077 and 6,224,628). Although improved, the extreme thinness of the lens manufactured in accordance with U.S. Pat. No. 6,096,077 caused some minor distortions of the optic once in the eye, while the lens manufactured in accordance with U.S. Pat. No. 6,224,628 was poured of molded silicone and did not provide the desired visual acuity.

Generally, the lens separates the aqueous humor from the vitreous body. The iris separates the region between the cornea or anterior of the eye and the lens into an anterior chamber and a posterior chamber. The lens itself is contained in a membrane known as the capsule or capsular sac. When the lens is removed from the eye, the capsule may also be removed (intracapsular extraction), or the anterior portion of the capsule may be removed with the lens leaving the posterior portion of the capsule intact (extracapsular extraction), often leaving small folds or flaps from the anterior portion of the capsule. In an intraocular implant, the artificial or prosthetic lens may be inserted in the anterior chamber, the posterior chamber, or the capsular sac. The artificial lenses are usually fixedly attached within the eye, either by stitching to the iris, or by some supporting means or arms attached to the lens; in all cases the fixation mechanisms are categorized as haptics.

Several intraocular lenses designed for implant in the anterior chamber feature haptics with feet which support the lens in order to avoid the need for clips or sutures to secure the lens to the iris. The lenses worked; however, sizing the lens to fit the eye was critical to avoid complications. The lenses were made in lengths from 11.5 mm to 14 mm in 0.5 mm increments, and the thickness of the feet was about 250 microns.

A variety of lenses has been developed that provides up to four point support for the lens. The support structures for these haptics are often linked to the lens body so that the support structure should not deflect freely of the lens body, and therefore be liable to irritate portions of the eye in contact with the support structure. A variety of shapes and geometries for the lens supporting elements, or haptics, has been disclosed and described (U.S. Pat. No. 4,254,510; U.S. Pat. No. 4,363,143; U.S. Pat. No. 4,480,340; U.S. Pat. No. 4,504,981; U.S. Pat. No. 4,536,895; U.S. Pat. No. 4,575,374; U.S. Pat. No. 4,581,033; U.S. Pat. No. 4,629,460; U.S. Pat. No. 4,676,792; U.S. Pat. No. 4,701,181; U.S. Pat. No. 4,778,464; U.S. Pat. No. 4,787,902; U.S. Pat. No. Re. 33,039; U.S. Pat. No. 4,872,876; U.S. Pat. No. 5,047,052; U.K. Patent No. 2,165,456).

Despite the advances, there remain problems with intraocular implants. For example, when an intraocular lens is inserted in the eye, an incision is made in the cornea or sclera. The incision may cause the cornea to vary in thickness, leading to an uneven surface which can cause astigmatism. The insertion of a rigid lens through the incision, even with compressible haptics, requires an incision large enough to accommodate the rigid lens (typically at least 6 mm), and carries with it the increased risk of complications, such as infection, laceration of the ocular tissues, and retinal detachment. Deformable intraocular lenses made from polymethylmethacrylate (e.g. "PMMA"), polysulfone, silicone or hydrogel may be inserted through a smaller incision, about 4 mm.

It is preferred that the intraocular lens be capable of insertion through a small incision. U.S. Pat. No. 4,451,938 shows an intraocular lens in which the lens body is made in two pieces so that each piece may be inserted through the incision separately and then joined by dowels after insertion in the eye. U.S. Pat. No. 4,769,035 discloses a foldable lens which may be inserted through an incision about 3.5 mm in length.

When the intraocular lens is inserted in the anterior chamber of the eye, the feet of the haptics, or lens supporting elements, generally lodge in the scleral sulcus, a depression anterior to the scleral spur where the iris and the ciliary muscle join the sclera in the angle of the anterior chamber. The scleral sulcus is crossed by trabecular tissue in which are located the spaces of Fontana. The anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The lens should be positioned so the flow of fluid through the trabecular tissue is not blocked or glaucoma may result.

Since the feet of the haptics of anterior chamber lenses rest in the scleral sulcus, the flow of fluid is blocked where the feet are in contact with the trabecular tissue. It is therefore desirable to decrease the amount of surface area of the haptic foot in contact with the trabecular tissue. At the same time, the haptic feet have sufficient height to prevent adhesive tissue or synechia from growing around the feet and anchoring them to the iris or cornea. The opening of the trabecula is about 200 microns, and the haptic feet of conventional intraocular lenses are usually on the order of 175 to 200 microns, effectively blocking the openings in the trabecula wherever the feet are in contact with the tissue.

Other lenses that are situated in the posterior chamber may attach to the ciliary sulcus or be positioned in the equator of the capsular sac. In haptics with attachment to the ciliary sulcus, appropriate dimensioning is essential to ensure proper anchoring. In haptics with attachment to the capsular equator, recent science demonstrates the need for appropriate dimensioning also, as the haptic must place the lens properly in the capsule. If the haptic is too short for the capsule, the lens can dislodge or rotate in the eye, events that can require additional surgery to correct and can also cause intraocular trauma. Additionally, haptics that are too short for the capsule do not allow the lens to provide the patient with any desired or designed focal flexibility (that is, accommodation). If the haptic is too long for the capsule, the lens can angle either posteriorly or anteriorly at a greater angle than designed, in the former case significantly reducing visual acuity at distance and risking reverse accommodation, in the latter case putting pressure on the iris and diminishing focal flexibility.

U.S. Pat. Nos. 5,258,025 and 5,480,428 describe a lens surrounded by a sheet-like "positioner" having projections called "supporting elements either at the four corners of or continuously around the positioner, the supporting elements being 0.3 mm long and 0.01 to 0.05 mm thick (7"a and 7"b of FIG. 3 of the '025 patent, 18 of the '428 patent). However, the lens is for implantation in the posterior chamber, the lens of the '428 actually having a length short enough to "float." In addition, the sheet-like nature of the positioner prevents independent deflection of the feet in response to forces applied by the eye.

In addition, the lens may place a greater or lesser degree of force on the haptic feet as the lens is compressed, depending upon construction of the lens. Since the amount of pressure for a given surface area is proportional to the force, it is desirable to decrease or distribute the amount of force placed on the haptic feet in order to diminish the force applied by the feet on the trabecular tissue. This goal is achieved by mounting the haptic arms on the ends of a flexible support bar in cantilever fashion, the support bar being offset from the lens body by a stem.

The act of surgically removing the natural lens and replacing it with an intraocular lens of whatever design gives rise to certain other possible conditions that can have a profound impact on the patient's ability to see clearly over a protracted period of time, the extent of focal accommodation that can be provided to the patient, and the effective positioning of the replacement lens in the eye. These conditions normally occur in a majority of cases but may be able to be mitigated with inventive lens and haptic designs. In particular, ophthalmologists have observed that the lens capsule will tend to atrophy over time. This is in part attributable to the fact that the replacement lens rarely occupies the entire lens capsule, and most lenses tend to flatten out the capsule, thus allowing the anterior and posterior surfaces of the capsule to adhere together, causing capsular atrophy, hardening, and adhesions. All these will necessarily diminish the effectiveness of any lens claiming to offer focal accommodation. It is possible that increased circulation of the aqueous humor can preserve the suppleness of the natural lens capsule, and preventing contact between the capsular surfaces should prevent capsular adhesions.

Some physicians have advocated the use of capsular retention rings to prevent capsular atrophy. However, these rings, which are situated in the lens equator and generally used only during the surgical procedure, do not allow the ciliary body to influence the dimensions of the lens so as to provide for focal accommodation. Thus, whereas capsular retention rings may be effective when used in conjunction with non-accommodating lenses, their value with premium lenses that claim accommodation is questionable.

In some cases post surgical adhesions can occur between the lens capsule and the haptic of the intraocular replacement lens. If significant enough, these adhesions can diminish the focal accommodative functions of the lens.

Posterior Capsule Opacification (PCO) is a condition that occurs in approximately 50% of cataract patients within three years after surgery. PCO is caused by the natural migration of epithelial cells from the anterior lens capsule to the equator, thence to the posterior surface. Once the epithelial cells reach the equator, the cells die off leaving proteins that accumulate on the posterior capsular surface in the form of Elschnig's pearls or of fibroblasts that athere to the capsule and can cause significant fibroblasts, shrinkage, and clouding of the lens. If the PCO migrates to the optical area of the capsule, vision is significantly impaired. The occurrence of PCO can be mitigated surgically by means of Nd-YAG-Laser correction, which perforates the posterior capsule with small holes that deter the PCO from further migration. However, Nd-YAG laser capsulotomy surgery also carries risks of post-surgical complications including possible incursion of the vitreous into the capsule, and, as such, should be avoided if possible.

In the case of the inventive haptic designs incorporated herein, the inventors believe that the onset of PCO may be delayed or eliminated altogether through the use of appropriate haptic design to deter epithelial cell migration. In particular, 1) the design of an ultra-thin fixation plate and its appropriate sizing to fit securely at the capsular equator is intended to arrest epithelial cell migration at the haptic attachment zone and mitigate PCO accordingly, 2) a haptic design that keeps the capsule open and prevents contact between the anterior and posterior surfaces may assist in mitigating PCO onset by maintaining hydration of the capsule, 3) the quality of the cataract or CLEAR surgery can assist in retarding PCO through assiduous cleaning and polishing of the anterior capsule, and 4) the positioning of certain retention rings in the capsule, whether at the capsular equator, against the surface of the anterior capsule, and/or against the surface of the posterior capsule may arrest the migration of epithelial cells and prevent their aggregation in the posterior capsular optic zone. In some cases, IOL designers have found some success at mitigating the onset of PCO by configuring the posterior surface of the lens so as to provide a right angle at the junction of the lens with the posterior capsule. This configuration is particularly applicable for those lenses that rest entirely against the posterior capsule and do not accommodate. In other cases, IOL designers have determined that the surface quality of the haptic may have some influence on PCO mitigation.

SUMMARY OF THE INVENTION

The present invention overcomes the problems and disadvantages associated with current strategies and designs and provides new haptic devices and methods for positioning an intraocular lens in the eye, as well as designs for specific functionality to provide optimal focal flexibility and mitigate common post surgical problems.

One embodiment of the invention is directed to haptic devices that attach to the side of an edge of a lens and at a distance from the center of the lens. Preferably the haptic has a first haptic contact point that breaks the plane of a line passing through the center of the lens at about preferably 60 degrees from preferably the twelve o'clock position of the lens and a second haptic contact point that breaks the plane of a line passing through the center of the lens at about preferably 300 degrees from the twelve o'clock position of the lens. Preferably, the haptic arm center line is an extension of the planes passing through the lens at 60 and 300 degrees and extends to intersect a circle where the center is the center of the lens and the radius is greater than the radius of the lens. Also preferably, a radially distant end connects to an arm that intersects the outside diameter of the haptic at an offset point parallel to the 12 o'clock plane of the lens.

Preferably, the haptic is designed to affix to the lens on each side of the optic edge at a sixty degree angle from the center meridian of the lens. The haptic arm is a band of the haptic material that extends outward from the optical connection then curves back inward to connect with a solid arc of haptic material concentric with the optical edge of the lens and at a distance from such optical edge to provide for a kidney-shaped open section between the lens and such haptic material. The material of the haptic is preferably flexible, thus the haptic design provides for greater thickness of the haptic in the anterior/posterior plane so as to allow for suitable positioning of the lens in the eye without anterior-posterior dislocation. The ends of the haptic may be solid, with the fixation portion of the haptic thinner or thicker than the band of material at the optical connection. Additionally, the design of the haptic at its fixation point to the capsule is intended to allow the anterior and posterior rim of the capsule to fixate to the haptic at such point(s), thus inhibiting the migration of epithelial cells from the anterior to the posterior capsule, thereby mitigating Posterior Capsule Opacification. In another embodiment, the arms of the haptic are modestly arched to increase focal flexibility.

Another embodiment of the invention is directed to haptic devices that are kidney shaped, wherein a portion of the haptic end is solid. Preferably, the solid portion of the end is thinner than the remaining portion of the haptic. The haptic may further comprise a notch at the 12 o'clock position radially proximal that allows for bending. The functionality of the inventive haptic is to anticipate natural post-surgical capsular atrophy while maintaining both a firm attachment of the haptic at the capsular equator and central positioning of the lens optic in the capsule.

Another embodiment of the invention is directed to haptic devices that are kidney shaped, wherein a portion of the haptic end is solid. Preferably, the solid portion of the haptic is configured so as to extend forward to meet the anterior capsule at some distance from the equator, and posteriorly to meet the posterior capsule also at some distance from the equator. The haptic may further comprise a notch at the 12 o'clock position radially proximal that allows for bending. The haptic may also comprise a series of small notches at the inner radius of the anterior and/or posterior feet to allow for flexing in natural response to motions of the ciliary body as well as natural differences in capsular size. The functionality of the inventive haptic is to mitigate the onset of natural post-surgical capsular atrophy by maintaining the capsule open at the equator. This should provide for enhanced circulation in the capsule of aqueous solution, which may maintain suitable levels of hydration to preserve capsular flexibility. This also may inhibit the tendency of the anterior and posterior capsules to adhere to each other, a common post-surgical occurrence with other haptic designs. Another functionality of the inventive haptic is to provide positioning of the haptic feet so as to respond to the natural flexing and stretching of the lens capsule in response to ciliary body actions, while maintaining both a firm attachment of the haptic to the capsule, and central positioning of the lens optic in the capsule.

Another embodiment of the invention is directed to haptic devices that have some open sections between the haptic feet and the optic and with haptic feet that comprise rings, arced anteriorly and posteriorly with respect to the plane of the lens optic, such that the anterior ring makes contact with the anterior capsule at some distance from the lens equator, and the posterior ring makes contact with the posterior capsule at some distance from the lens equator, the rings connected to each other and to the framework supporting the lens optic by means of ribbons and struts that maintain suitable spacing between the rings and provide for proper positioning of the lens within the capsule. The functionality of the anterior ring is to arrest epithelial cell migration across the anterior capsule, thus preventing these cells from maturing and arriving at the capsular equator. Another functionality of the inventive anterior ring is to respond to the changes of the ciliary body in such a manner as to enable the forward motion of the lens optic within the capsule to accommodate for near vision. The functionality of the posterior ring is to protect the posterior optic zone from PCO by maintaining a suitable barrier between any pearls or fibroblasts that may develop over time and block their incursion into the area behind the lens optic. Another functionality of the posterior ring is to capture the physical forces fo the ciliary body and work in conjunction with the anterior ring, the struts and the ribbons of the haptic to allow the lens optic to move within the capsule to adjust to the various stages of focal accommodation. Another functionality of the posterior ring, together with the anterior ring, the struts and ribbons is to maximize the natural circulation of the aqueous humor so as to preserve hydration throughout the lens capsule and the aqueous humor. This hydration may have the additional desirable effect of providing a mechanism whereby the spent and arrested epithelial cells can be flushed away by the aqueous humor and disposed of through the trabecular meshwork.

Another embodiment of the inventive haptic is a solid circle haptic into which are cut arced channels, preferably five, that extend from the anterior ring to the edge of the optic. These channels allow the optic to move in accommodation without distortion or decentralization, while the anterior and posterior haptic rings fix the lens centered in the capsule and maintain the capsule open.

Another embodiment of the invention is directed to haptic design to work with injectors for surgically injecting the lens and haptic into an eye of a patient. Preferably the patient is a mammal and more preferably the mammal is a human. The haptic to be injected is capable of being compressed to allow insertion into the eye. Preferably, an outer portion of the haptic is compressed into a pointed shape to aide travel through an injector and entry into the eye, and a flexible portion is thicker in the anterior or posterior plane and allows the haptic to flex for positioning within the eye without anterior/posterior movement. Also preferably, the top of the proximal end of the solid portion is attached to the bottom of the haptic portion creating an offset between the solid and flexible portions of the haptic. The distal end is capable of resting in the equator of the capsule when inserted into the eye that contained the natural lens and the posterior zonules of the eye rest against the capsule. Once position in the eye, the force created by the movement of the ciliary processes of the eye is capable of moving the zonules toward a prime meridian of the eye, the zonules in turn transfer force through the capsule that contained the natural lens and to the end of the solid portion of the haptic. The haptic is preferably capable of transferring force to the end of the flexible portion of the haptic, where the offset creates an upward, rotational force along the haptic, in turn advancing the lens forward within the eye. Also preferably, the top of the proximal end of the solid portion is attached to the bottom of the haptic portion creating an offset between the solid and flexible portions of the haptic. The distal end is capable of resting against the anterior surface of the capsule when inserted into the eye that contained the natural lens and the posterior end rests against the posterior surface of the capsule. Once positioned in the eye, the force created by the movement of the ciliary processes of the eye is capable of moving the zonules toward a prime meridian of the eye, the zonules in turn transfer force through the capsule that contained the natural lens and to the end of the haptic feet. The haptic is preferably capable of transferring this force through a series of struts that connect the anterior ring to the posterior ring and to the end of the flexible portion of the haptic, where the offset creates a forward, force along the haptic, in turn advancing the lens forward within the eye.

Another embodiment of the inventive haptic is to provide for a series of easements in the struts connecting the anterior and posterior haptic rings whereby the level of force exercised on the lens is commensurate with the desired degree of accommodative movement of the lens within the eye.

Another embodiment of the invention is directed to a haptic of the invention and further comprising a second haptic to be localized 180 degrees from the first haptic when inserted into the eye. Preferably the lens and the haptic are essentially in the same anterior posterior plane. When positioned in the eye, forward movement of the lens creates the ability to see near objects from a single focal plane lens. When the lens is positioned anteriorly to the distal end of the haptics, it creates a positive vault, and when positioned posteriorly to the distal end of the haptics, it creates a negative vault.

Another embodiment of the invention is directed to a haptic, wherein a portion of the haptic is flexible and arched when inserted into an eye to where the zonules of the eye transfer force against the solid portion of the haptic creating an upward force vector, which in turn would move the lens optic anteriorly. If the haptic is a plat haptic at its contact point with the lens equator, there is a reduced amount of clearance between the anterior and posterior surfaces of the natural lens capsule allowing the surfaces to grow together. In this case, the attached capsular surfaces and the edge of the haptic form an opening small enough to significantly reduce cell migration from the equatorial region of the capsule. If the haptic used has anterior and posterior rings, there is a stable amount of clearance between the anterior and the posterior surfaces of the lens capsule preventing the surfaces from growing together. The angle of the negative vault and the angle of the radius between the prime meridian and the optic edge are preferably equal. Also preferably, equal angles create a tangent between the capsule that contained the natural lens and the edge of the optic of the lens. When inserted into the eye, tangential forces use the capsule to seal the edge of the lens preventing cell migration under the lens.

Another embodiment of the invention is directed to a haptic wherein sections of the haptic are angled and connected by joints such that the optic rests posteriorly in the capsule for distance vision and the joints, flexing or stretching in response to the movement of the ciliary body, moves the lens anteriorly for near vision. Preferably, there are rings attached to the angled joints or segments that rest on the anterior and/or posterior surfaces of the capsule, maintaining a distance between such anterior and posterior surfaces thereby providing for continuous natural hydration of the capsule and circulation of the natural fluids of the aqueous humor. Also preferably, such rings arrest substantially the migration of epithelial cells on the anterior capsule and the proliferation of posterior capsular opacification in the focal range of the lens.

Another embodiment of the invention is directed to a method of securing a lens in a mammalian eye comprising removing a natural lens from a mammalian eye; and inserting a lens comprising the haptic of the invention into the mammalian eye.

Another embodiment of the invention is directed to devices, such as insertion devices, and methods of inserting a haptic into a lens envelope of a mammalian eye comprising the haptic of the invention.

Other embodiments and advantages of the invention are set forth in part in the description, which follows, and in part, may be obvious from this description, or may be learned from the practice of the invention.

DESCRIPTION OF THE DRAWINGS

FIG. 13. Second iteration of curved ribbon (open looped) haptic in distance position.
FIG. 14. Second iteration of curved ribbon (open looped) haptic in near accommodation position.

DESCRIPTION OF THE INVENTION

The haptic device is used to affix an intraocular lens within the lens capsule once the natural crystalline lens has been removed surgically. The three specific design purposes of the haptic are: i) to permit the lens to be implanted in the eye by means of a special injector through an incision of less than about 3 mm; ii) to allow the lens to move within the posterior chamber of the eye in order to provide focal flexibility to the patient; and iii) to affix the lens in the equator of the lens capsule in such a way as to minimize the risk of Posterior Capsule Opacification ("PCO"), a negative consequence of lens replacement procedures that currently occurs in approximately 50% of patients within 2 to 3 years after surgery. Although intraocular lenses have been successfully implanted for several decades now, many of the haptic designs do not produce the desired results of mitigating PCO and/or facilitating focal flexibility (or the ability of the patient to adjust far to near vision and minimize the need for reading glasses).

Figure 7:
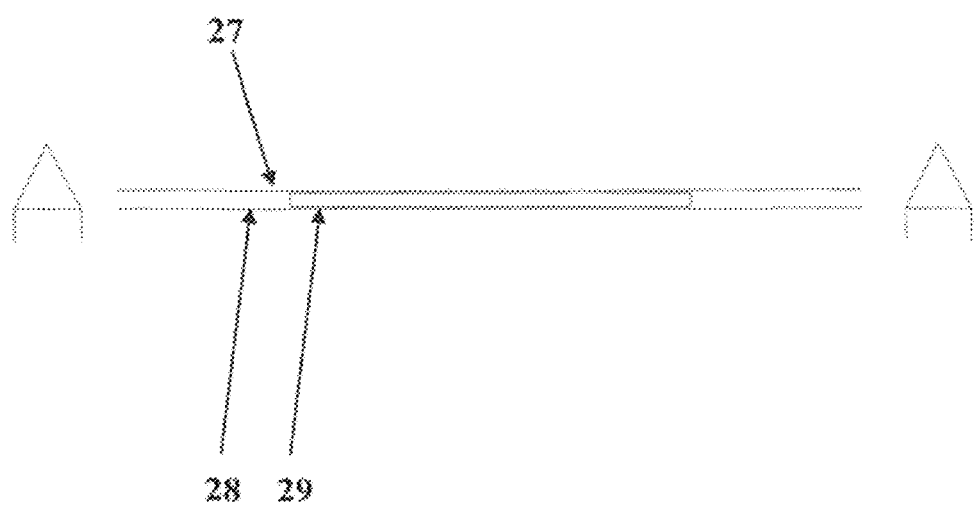
FIG. 7. Cross sectional area of haptic end.

A haptic device design has been surprisingly discovered that that ameliorates PCO and facilitates focal flexibility (or the ability of the patient to adjust far to near vision and minimize the need for reading glasses). In one embodiment, the haptic of the invention is secured to the equator of the lens capsule by means of a solid but very thin plate of the same material as the attached lens, which preferably may be any of polymethylmethacrylate, hydrophobic or hydrophilic acrylate, silicone, or blends of these materials (or of the same material as the lens). The width of the plate is designed to extend beyond that portion of the lens envelope that typically closes post-removal of the natural lens (FIG. 7). Epithelial cells, normally found on the anterior surface of the inner lens capsule, can migrate to the posterior surface if their path is not impeded. A purpose of the design of the haptic of the invention is to cause a tighter closure at the edge of the haptic, which inhibits ongoing migration and growth of the epithelial cells. Moreover, the width and breadth of that portion of the haptic helps preclude migration of such epithelial cells across the anterior portion of the lens capsule to the equator. While this design may not altogether remove the risk of PCO, it retards PCO growth substantially.

A second haptic device design has been surprisingly discovered that that ameliorates PCO and facilitates focal flexibility (or the ability of the patient to adjust far to near vision and minimize the need for reading glasses). In one embodiment, the haptic of the invention is secured to the anterior capsule with an arced anterior foot, and to the posterior capsule with an arced posterior foot the effect of which is to maintain a space between the anterior capsule and the posterior capsule so as to provide for ongoing hydration of the lens capsule by the fluids of the aqueous humor. The connection between the arced anterior foot and the arced posterior foot is made by a series of struts, which may have some easements cut into them, that maintain the desired distance between the anterior and posterior feet of the haptic and optimize the accommodative force on the optic of the inventive lens, while providing for adequate fluid circulation within the capsule and the posterior chamber of the aqueous humor. Epithelial cells, normally found on the anterior surface of the inner lens capsule, can migrate to the posterior surface if their path is not impeded.

In another embodiment (depicted in FIGS. 23*a-b*), a haptic design has been surprisingly discovered that has anterior 2335 and posterior 2330 haptic feet that comprise entire rings that rest on the anterior and posterior capsules, respectively, maintaining the entire capsule open and creating a barrier at both the anterior and the posterior capsular surfaces to prevent migration of epithelial cells. In this embodiment, the haptic feet are connected by a series of struts 2315 that have open spaces 2320 between, preserving the designed distance between the rings and providing for optimal fluid circulation around the inventive lens. In this embodiment also, the anterior 2335 and posterior 2330 rings may be configured so as to arrest epithelial cell migration across the anterior capsule and incursion of PCO into the optical zone of the posterior capsule, thereby providing the potential for the patient to use the intraocular lens for a substantial period of time without adverse consequences. In this embodiment, easements may be made in the struts to accommodate smaller than normal capsules, thus providing for stable concentration of the lens optic notwithstanding potential capsular size differences or changes over time. In this embodiment additionally certain easements may be made in the inner surface of the anterior 2335 and posterior 2330 rings so as to provide for responsiveness of the lens haptic to the muscular prompts of the ciliary body.

In another embodiment, the haptic of the invention may be constructed principally of a ribbon of the same material as the attached lens (as described herein). The open framework design of this portion of the haptic is to hold the optic centered vis-à-vis the retina while responding to the motion of the ciliary body so as to move the optic forward and backward in the eye, much in the same manner as a natural lens, with a minimum of lateral or oblique distortion. In the variation of this haptic design as set forth in FIG. 5, the arched portion of the haptic further facilitates the focal flexibility and causes the optic of the lens to move anteriorly as the patient focuses on near objects.

In these embodiments, the entire dimension of the lens, including both haptics and the optic, preferably varies depending upon the measurement of the natural lens capsule. The haptic has varying points of individual tailoring, including the length of the ribbon haptic (2) and (3), and the dimension of the solid end portion of the haptic. Additionally, the haptic may be used for veterinary purposes, and its overall dimensions may be increased or reduced to fit in the lens capsule of various animals.

The following examples illustrate embodiments of the invention, but should not be viewed as limiting the scope of the invention.

EXAMPLES

Figure 1:
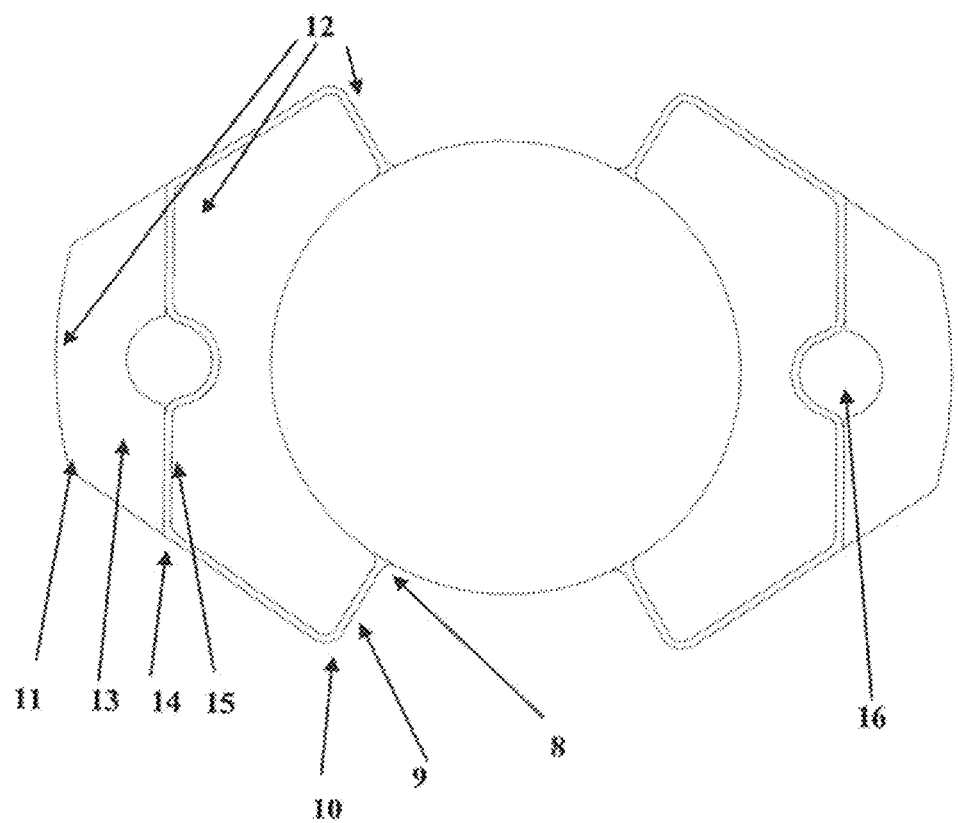
FIG. 1. Top view of lens with haptic.
Figure 2:
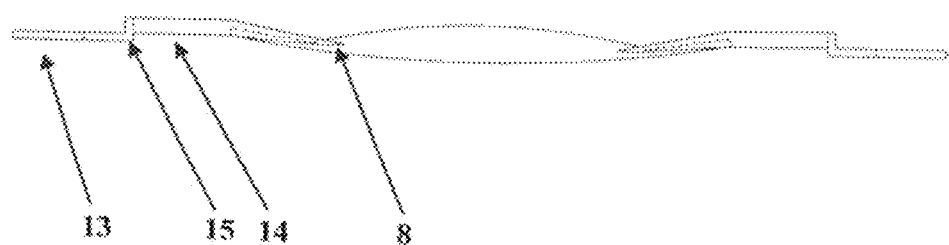
FIG. 2. Sagittal view of lens with haptic.

Depicted in FIG. 1 is a top view of an intraocular lens with a haptic device, and FIG. 2, a sagittal view. The haptic attachment point 8 to optic is shown along with a ribbon shaped haptic extension 9 which is in a plane through the center of the optic and the attachment point. The ribbon shaped haptic arm intersection with a circular plane larger than the radius of the optic. The solid end portion of the haptic 13 intersects the outside diameter of the lens at a point that is parallel to a plane passing through the 12 o'clock and 6 o'clock positions of the lens. The overall shape of the haptic resembles a kidney with sharper curves where the lens optic makes up a portion of the kidney. Solid end portion 13 of the haptic is thinner than the ribbon shaped sections 9.

As depicted in FIG. 1, ribbon shaped haptic 9 lies between the solid portion 13 and the end of the extended arm 8. The ribbon shaped section of the haptic 9 is shown above the solid portion of the haptic 13 in FIG. 2. Also, along the bottom, the ribbon shaped haptic 9 attaches to the solid haptic 13 along the edge (proximal to the optic) of solid portion of the haptic 13. FIG. 1 shows the notch 16 which is cut into solid haptic portion 13 to allow easy flexing for deformation into an injector.

Figure 3:
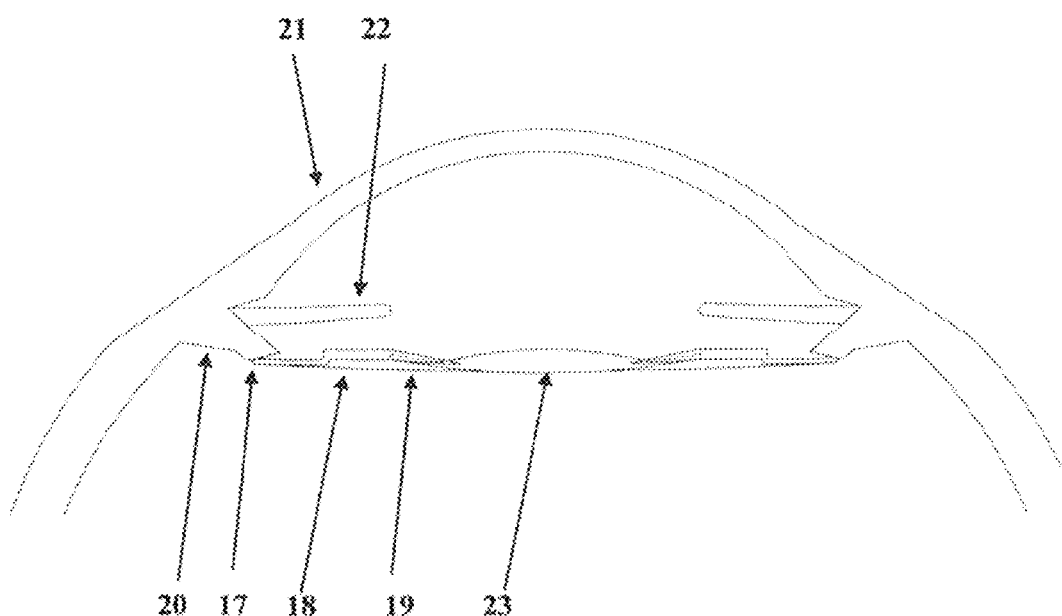
FIG. 3. Ciliary process for distance vision.

As depicted in FIG. 3, the tip 17 of the lens haptic rests against the equator of the capsule which is held in position by the zonules. Zonules are the hair like structures that attach to the natural lens and the ciliary body and hold the natural lens in position. Zonules also aide in changing the shape of the natural lens for near vision. FIG. 3 also depicts the capsule 19 from which the natural lens was removed, and the ciliary body 20 of the eye that changes shape to allow the natural lens to change shape to give the patient near vision. The cornea 21 is the clear portion of the eye that refracts (bends) light. Along with the natural lens the light is bent to come to focus on the retina. The iris (colored portion) of the eye is used to meter the amount of light allowed in the eye.

Figure 4:
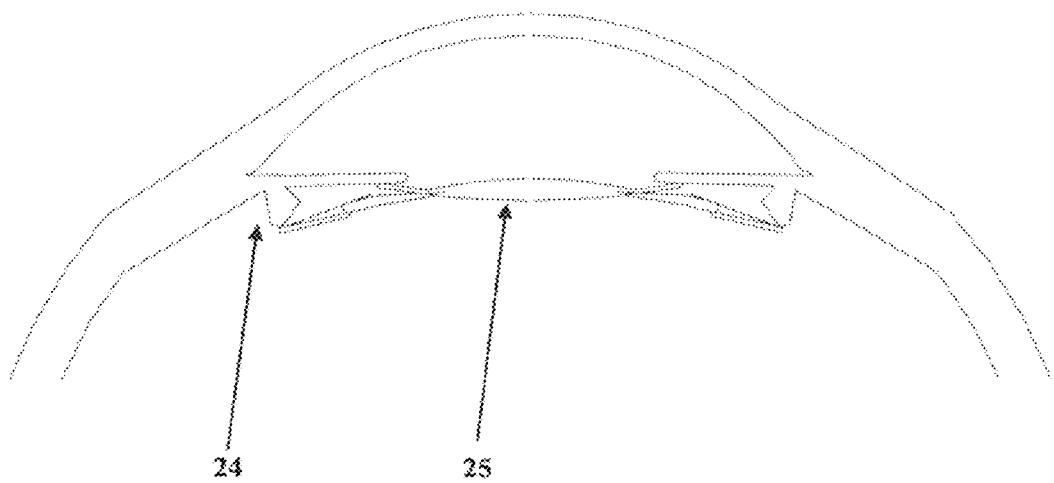
FIG. 4. Ciliary process for near vision.

As depicted in FIG. 3, the intraocular lens in the far position in the eye 23, whereas in FIG. 4, the ciliary body 24 moves and changes shape to provide near vision so that the intraocular lens is in the near position 25 in the eye.

Figure 5:
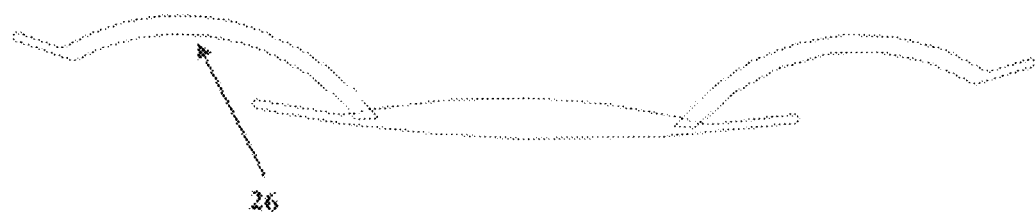
FIG. 5. Lens with arched haptic.

FIG. 5 depicts an arched haptic 26. As the ciliary body move force is applied to the tip of the haptic, which is transmitted into the arched haptic, which forces the haptic to compress and move anteriorly.

Figure 6:
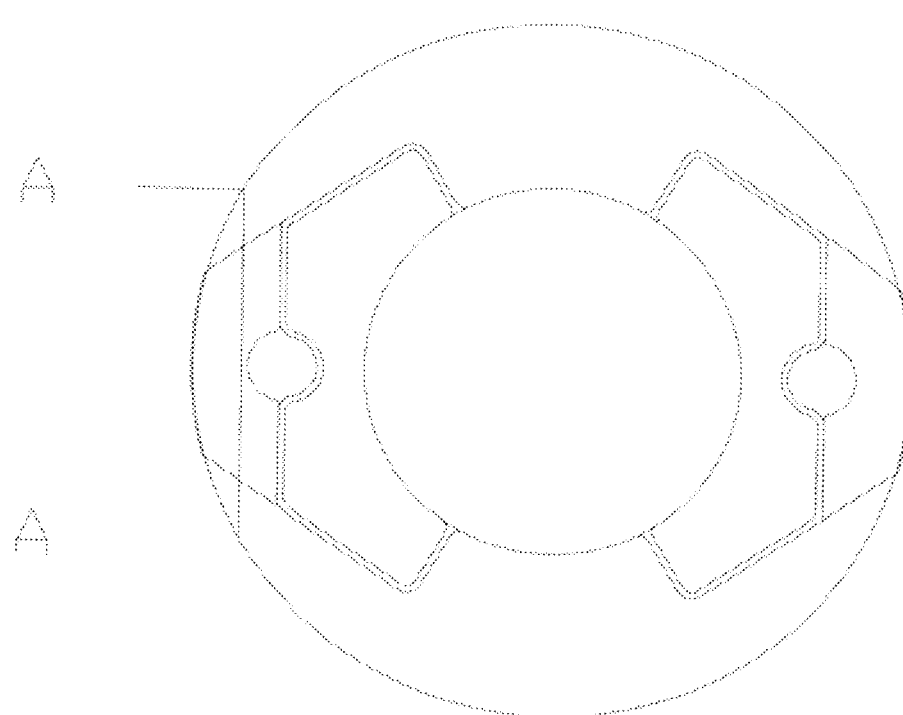
FIG. 6. Thin edge impedes posterior capsular opacification.
Figure 8:
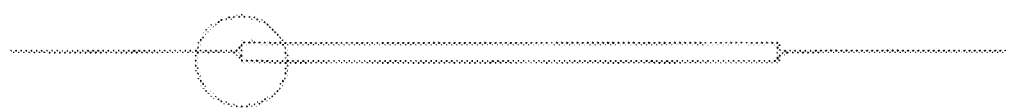
FIG. 8. Area of connection between haptic and lens to be enlarged.
Figure 9:
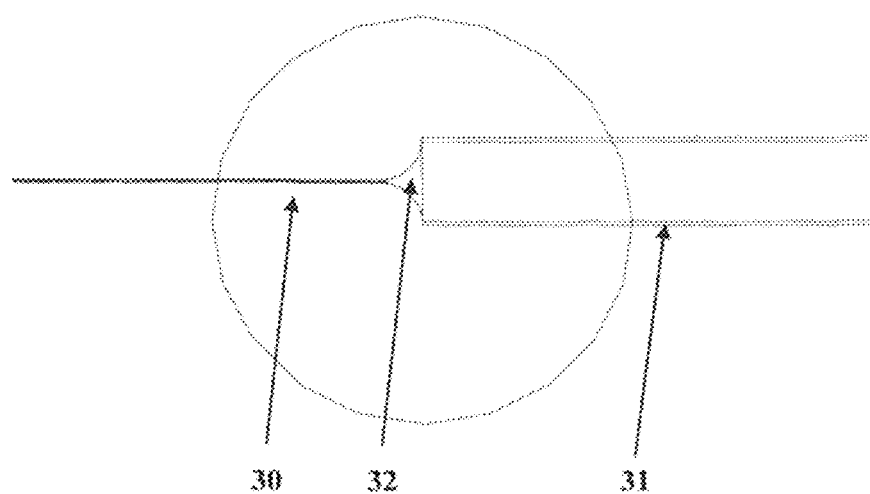
FIG. 9. Enlarged area of connection between haptic and lens.

As depicted in FIG. 6 is one embodiment of the haptic device and optic lens, demonstrating that area of the haptic (A-A) further delineated in FIGS. 7, 8 and 9, specifically designed to mitigate PCO. FIG. 6 addresses the circular formation, described by a continuation of the indicated arc ascribed to the haptic plate, indicating an approximation of the capsular equator and the lens position within the capsule.

Depicted in FIG. 7 is a cross-sectional area of the haptic end. Shown are the anterior section of the natural lens 27, the posterior section of the natural lens 28, and the intraocular lens haptic thin solid end portion 29.

Depicted in FIG. 8 are the anterior and posterior sections of the natural lens capsule as they grow together after surgery. Depicted in FIG. 9 is an enlarged portion of FIG. 8, showing the remaining tissue 30 surrounding the lens solid end 31 section stretched tight. The small opening remains 32 whereby cell growth movement through the opening is impeded. With thick footplates in many cases the opening is large enough that there is little or no impediment to the cell migration; therefore, the cells deposit between the intraocular lens and the posterior capsule which opacifies the capsule and reduces the light passage.

Figure 10:
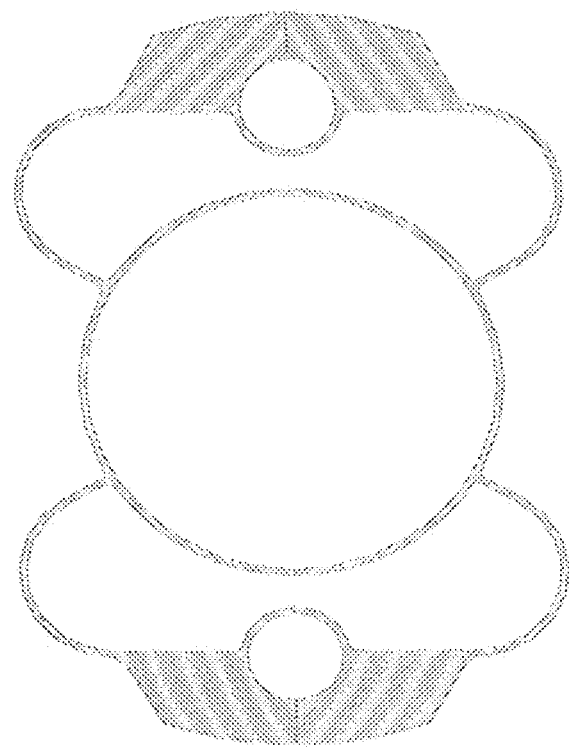
FIG. 10. Top View of Lens with haptic comprising curved ribbons to form the kidney shape.
Figure 11:
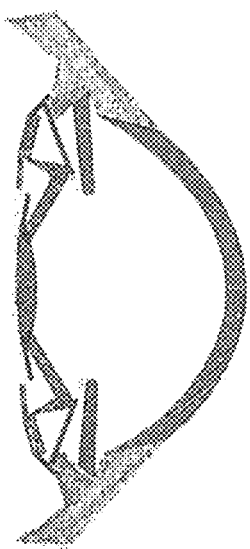
FIG. 11. Sagittal view of curved-open haptic in distance position.
Figure 12:
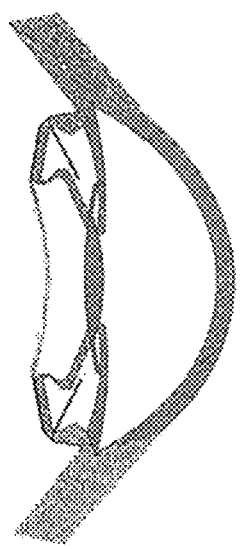
FIG. 12. Sagittal view of haptic with curved loops in near accommodation position.

Depicted as FIG. 10 is a top view of a haptic in which the angles have been removed providing for a continuous kidney shape in which the width of the ribbon haptic is less than the depth of that haptic so as to provide for natural easement and constant centering of the lens optic while ensuring sufficient thrust strength to move the optic anteriorly and posteriorly within the capsule to provide focal accommodation. FIGS. 11 and 12 are sagittal views of such a lens haptic, demonstrating a haptic design that is configured with two angles, as in a knee and an ankle, that respond to the force of the ciliary muscles to flex and extend, thus moving the lens optic.

As depicted in FIGS. 13 and 14, the innovative haptic contains one or more angled or arced segments providing additional flex and thrust for moving the lens within the eye to adjust for distance and near vision. The dimensions of the angled segments may vary in accordance with the designed purpose, and may be constructed such that the width of the segments may be varied or consistent while the depth of the segments will vary according to stress calculations for that segment such that the joints of the segments flex adequately to allow the length of the segments to exert the required force on the lens optic.

Figure 15:
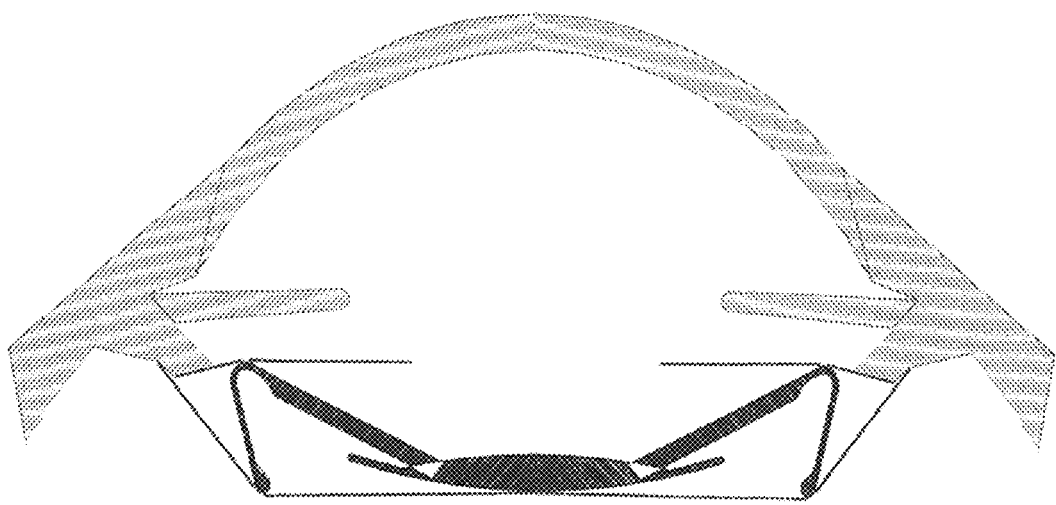
FIG. 15. Third iteration of open looped haptic in distance position.
Figure 16:
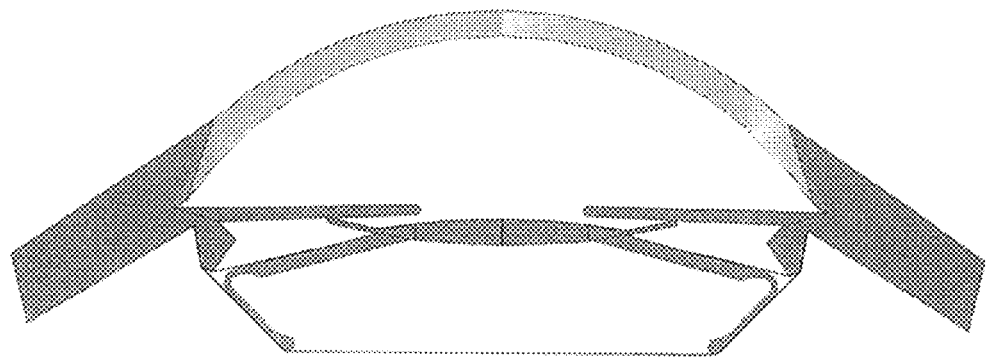
FIG. 16. Third iteration of open looped haptic in near accommodation position.

As depicted in FIGS. 15 and 16, the innovative haptic contains a knee and is designed such that the posterior foot of the haptic rests somewhat more central than the connection point of the knee with the anterior capsule.

Figure 17:
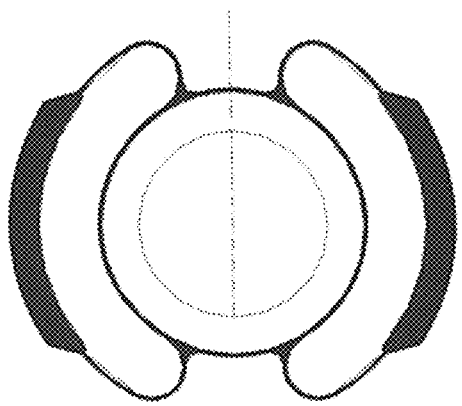
FIG. 17. Second iteration of open loop kidney ribbon haptic.
Figure 18:
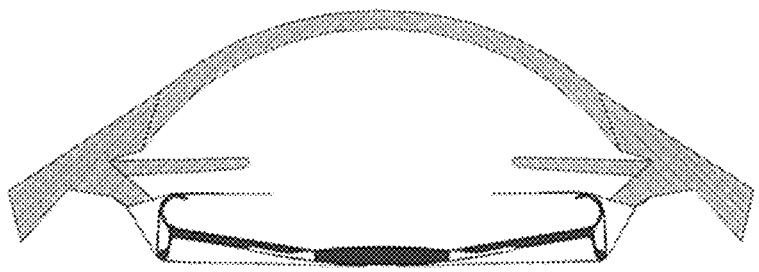
FIG. 18. Fourth iteration of haptic in distance position.
Figure 19:
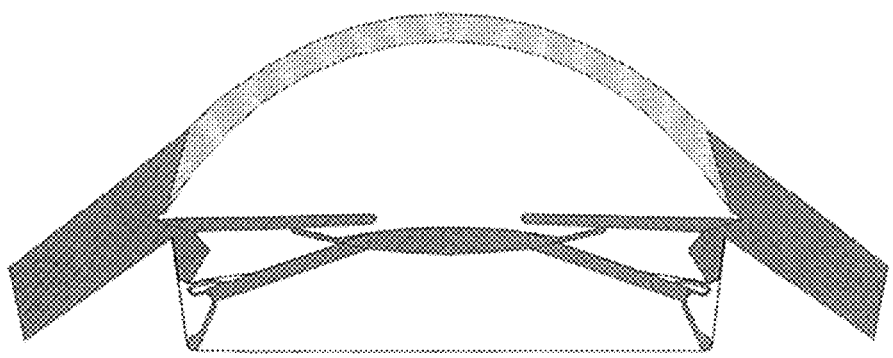
FIG. 19. Fourth iteration of haptic in near position.

FIG. 17 illustrates a further embodiment of the kidney haptic, with FIGS. 18 and 19 demonstrating the sagittal views of such haptic, in which case the anterior haptic plate is configured to curve anteriorly toward the center of the eye. The posterior foot of the haptic rests against the posterior capsule at a certain point somewhat outside the comparable contact point of the anterior haptic, though dimensions may vary in accordance with the designed purpose of such lens.

Figure 20A:
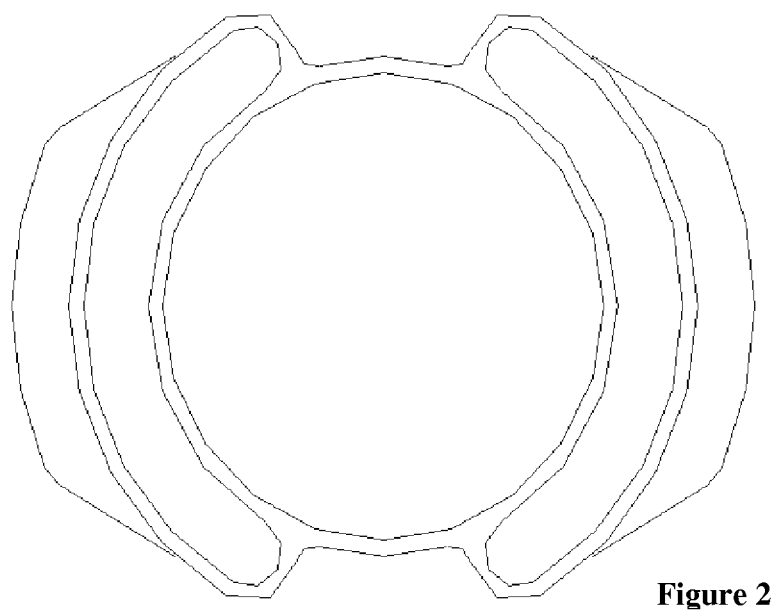
FIGS. 20*a-b*. Fifth iteration of open looped haptic with anterior and posterior feet in initial design specifications.
Figure 20B:
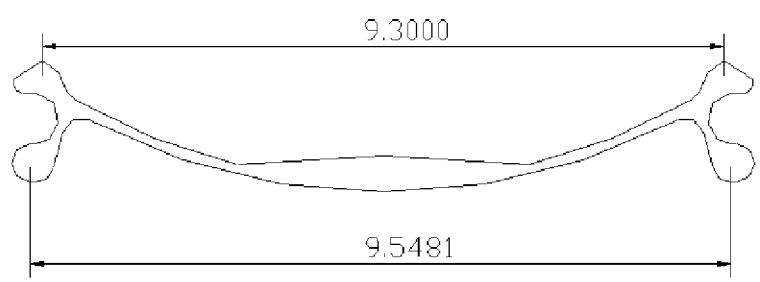
Figure 21:
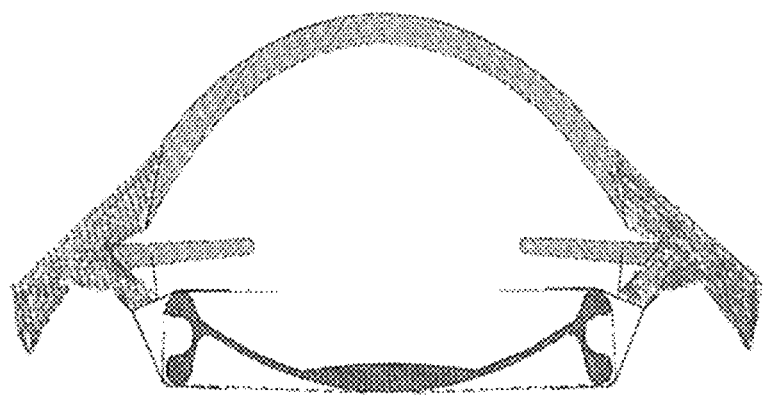
FIG. 21. Fifth iteration of open loop haptic in distance position.
Figure 22:
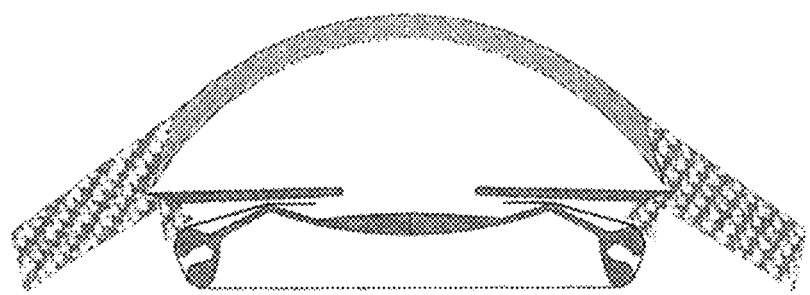
FIG. 22. Fifth open loop haptic in near accommodation position.

FIGS. 20a-b depict a further modification of the kidney haptic, showing a top view (FIG. 20a) and a sagittal view (FIG. 20b) with preliminary dimensions. FIGS. 21 and 22 illustrate the functionality of this inventive haptic in positions for distance and near vision.

In all of the above design manifestations, rings may also be affixed to the anterior and or posterior joints or legs of such angled segments to rest in the capsule at some distance from the equator, or with one ring in the equator and the other at some distance, to mitigate the migration of epithelial cells. In such cases the rings may contain right angles at the areas of contact with the anterior or posterior surface of the capsule. The function of such rings in conjunction with the angled segments may also be to maintain the aperture of the lens capsule distant from the equator so as to provide for continuous irrigation of the region by the normal circulation mechanisms of the aqueous humor. This may preserve the natural consistency and elasticity of the lens capsule, thus ensuring prolonged functionality of the inventive lens haptic.

Figures 23A, 23B:
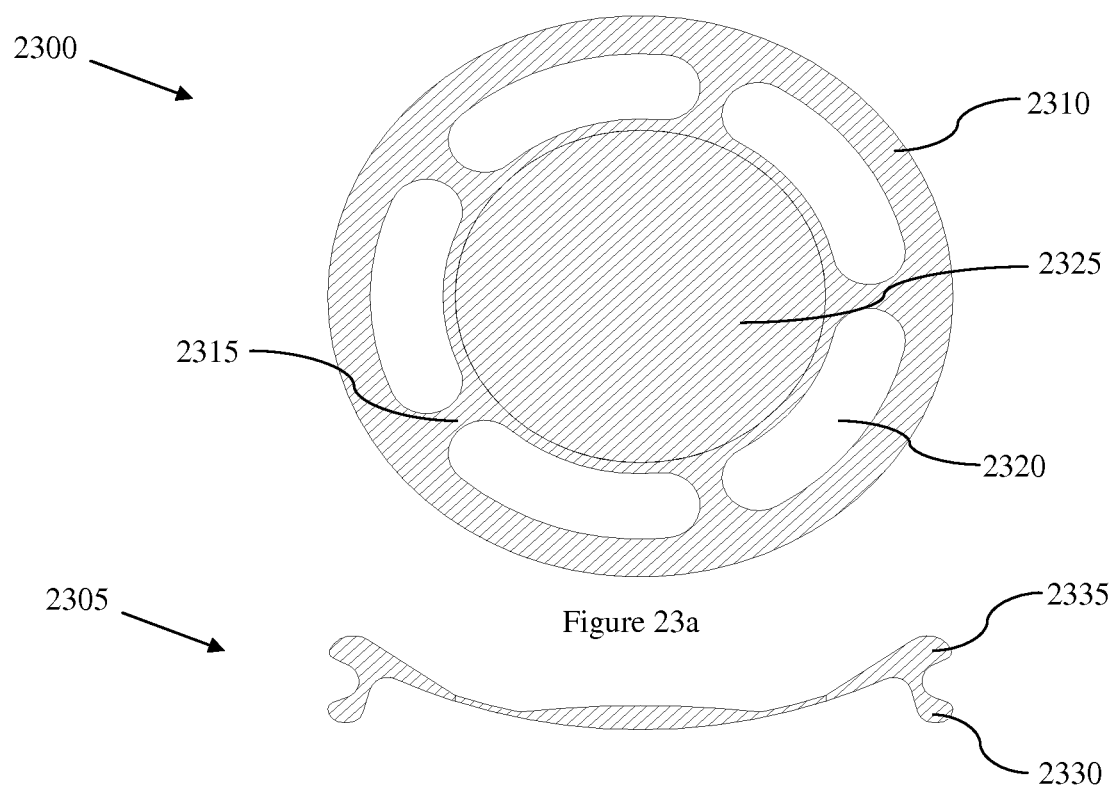
FIGS. 23*a-b*. Open Loop Haptic Design (Kidney haptic) with full anterior and posterior Rings.

FIGS. 23a-b depict both top 2300 and sagittal 2305 views of a full circular haptic with ribbons 2310 and struts 2315 to create oval openings 2320 between the optic 2325 and the haptic rings. The number of contained ovals and the precise configuration of such ovals may vary according to the designed intent of the inventive haptic. For example, as depicted in FIG. 23a, there may be five equally sized and equally spaced struts, wherein the width (measured radially on the haptic) of the ovals defined by the struts are smaller than the length of the ovals (measured circumferentially on the haptic).

Figure 24A:
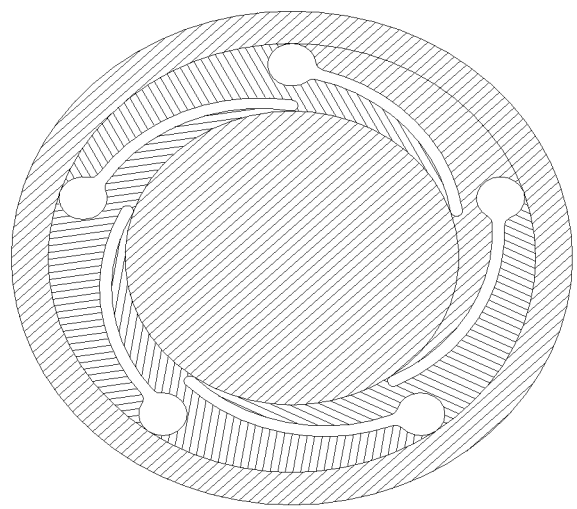
FIGS. 24*a-b*. Full circle haptic with arced grooves.
Figure 24B:

FIGS. 24a-b depict top and sagittal views, respectively, of a full circular haptic with arced grooves of material removed so as to provide for focal flexibility and fluid flow. In this case the number of grooves and the length and configuration of such grooves may vary in accordance with the intended purpose of the designed haptic.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A haptic of an intraocular lens comprising:
a single solid annular ribbon adapted to be placed within a capsular bag of an eye;
a plurality of struts directly coupled to both the annular ribbon and a circumference of a single optic, wherein the annular ribbon and the optic are coaxial and the annular ribbon is positioned at a distance from the circumference of the optic, wherein the plurality of struts define openings between the annular ribbon and the circumference of the optic, each opening having a smaller radial width than circumferential length; and
wherein the annular ribbon is comprised of an anterior haptic ring coupled to the plurality of struts, and a posterior haptic ring directly coupled only to the anterior haptic ring at an apex of a U-shaped recess in a radially outermost circumferential surface of the annular ribbon, wherein each of the anterior and posterior haptic rings is annular at the radially outermost circumferential surface, and wherein the posterior haptic ring is coupled posteriorly to the anterior haptic ring.

2. The haptic of claim 1, wherein an angle between each of the plurality of struts is 60 degrees.

3. The haptic of claim 1, wherein an angle between each of the plurality of struts is 72 degrees.

4. The haptic of claim 1, wherein the plurality of struts define ovular openings between the optic and the annular ribbon.

5. The haptic of claim 4, wherein there are five ovular openings.

6. The haptic of claim 1, wherein an inner radius of the annular ribbon is greater than the outer radius of the optic.

7. The haptic of claim 6, wherein each of the plurality of struts connects a point on an outside diameter of the optic to a point on an inside diameter of the anterior haptic ring.

8. The haptic of claim 1, which is capable of being compressed by an instrument to allow insertion into the eye.

9. The haptic of claim 8, wherein an outer portion of the haptic is compressible into a pointed shape to aide travel through an injector and entry into the eye.

10. The haptic of claim 1, wherein a number of struts of the plurality of struts is greater than or equal to five.

11. The haptic of claim 1, wherein a number of struts is less than five.

12. The haptic of claim 1, further comprising easements between the plurality of struts to reduce a mass of each of the plurality of struts.

13. The haptic of claim 1, wherein the haptic rings are positionable anteriorly or posteriorly within the capsular bag.

14. The haptic of claim 1, wherein the anterior haptic ring is positioned anteriorly from an anterior surface of the optic.

15. The haptic of claim 1, wherein, when inserted in the eye, a distal end of the haptic rests at an equator of the capsular bag.

16. The haptic of claim 1, wherein the annular ribbon, when inserted into the eye, is capable of moving in response to movement of a ciliary process.

17. The haptic of claim 16, wherein movement of the annular ribbon provides focal accommodation.

18. The haptic of claim 1, wherein, when inserted into the eye, the haptic significantly reduces cell migration from an equatorial region of the capsular bag in comparison to an intraocular lens without the haptic.

19. The haptic of claim 1, wherein the posterior haptic ring is a flange extending from the anterior haptic ring.

20. The haptic of claim 1, wherein the posterior haptic ring is capable of being coupled posteriorly to the anterior haptic ring prior to and post insertion into the eye.

21. A method of replacing a natural lens of a mammalian eye comprising:
removing the natural lens from the mammalian eye; and
inserting into the mammalian eye the haptic of claim 1.

22. A haptic of an intraocular lens comprising:
a single solid annular ribbon adapted to be placed within a capsular bag of an eye;
a plurality of struts directly coupled to both the annular ribbon and a circumference of a single optic, wherein the annular ribbon and the optic are coaxial and the annular ribbon is positioned at a distance from the circumference of the optic, wherein the plurality of struts define ovular openings between the annular ribbon and the circumference of the optic, each opening having a smaller radial width than circumferential length; and
wherein the annular ribbon is comprised of an anterior haptic ring coupled to the plurality of struts, and a posterior haptic ring directly coupled only to the anterior haptic ring at an apex of a U-shaped recess in a radially outermost circumferential surface of the annular ribbon, wherein each of the anterior and posterior haptic rings is annular at the radially outermost circumferential surface, and wherein the posterior haptic ring is coupled posteriorly to the anterior haptic ring.

* * * * *